United States Patent [19]

Nagano et al.

[11] Patent Number: 4,835,286
[45] Date of Patent: May 30, 1989

[54] 2-SUBSTITUTED PHENYL-4,5,6,7-TETRAHYDRO-2H-INDAZOLES

[75] Inventors: Eiki Nagano, Nishinomiya; Ichiki Takemoto, Toyonaka; Masayuki Fukushima, Takarazuka; Ryo Yoshida, Kawanishi; Hiroshi Matsumoto, Kakogawa, all of Japan

[73] Assignee: Sumitomo Chemical Company, Limited, Osaka, Japan

[21] Appl. No.: 23,386

[22] Filed: Mar. 9, 1987

Related U.S. Application Data

[60] Division of Ser. No. 717,088, Mar. 28, 1985, Pat. No. 4,670,043, which is a continuation-in-part of Ser. No. 536,528, Sep. 28, 1983, abandoned.

[30] Foreign Application Priority Data

Sep. 28, 1982 [JP] Japan ................. 57-170427
Nov. 6, 1982 [JP] Japan ................. 57-194893
Mar. 16, 1983 [JP] Japan ................. 58-45027

[51] Int. Cl.⁴ ........................................... C07D 231/00
[52] U.S. Cl. ..................... 548/369; 564/310; 71/92
[58] Field of Search .................. 548/369; 564/310

[56] References Cited

U.S. PATENT DOCUMENTS

| | | | |
|---|---|---|---|
| 3,867,452 | 2/1975 | Wilcox | 564/310 |
| 3,891,706 | 6/1975 | Wilcox | 564/310 |
| 3,935,315 | 1/1976 | Boesch | 564/310 |

Primary Examiner—Mary C. Lee
Assistant Examiner—Zinna Northington
Attorney, Agent, or Firm—Birch, Stewart, Kolasch & Birch

[57] ABSTRACT

Various intermediates useful in the production of herbicidal 2-substituted phenyl-4,5,6,7-tetrahydro-2H-indazole compounds are disclosed. These intermediates have the following formulas:

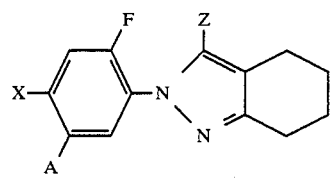

wherein X is chlorine or bromine, Z is chlorine or methyl, and A is amino, hydroxyl, or nitro;

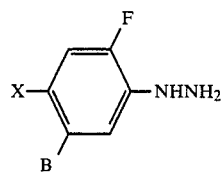

wherein B is nitro or hydroxy, and X is chlorine or bromine.

3 Claims, No Drawings

2-SUBSTITUTED PHENYL-4,5,6,7-TETRAHYDRO-2H-INDAZOLES

This application is a divisional of copending application Ser. No. 717,088, filed on Mar. 28, 1985, now U.S. Pat. No. 4,670,043, which is a continuation-in-part of Ser. No. 536,528, filed on Sept. 28, 1983, now abandoned.

The present invention relates to 2-substituted phenyl-4,5,6,7-tetrahydro-2H-indazoles (hereinafter referred to as "indazole(s)"), and their production and use.

The indazoles are represented by the formula:

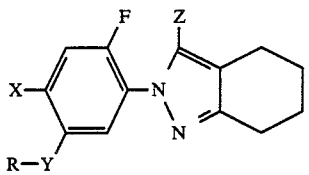

(I)

wherein X is a chlorine atom or a bromine atom, Y is an oxygen atom or an imino group, Z is a chlorine atom or a methyl group and R is a $C_2$–$C_4$ alkyl group, a $C_3$–$C_4$ alkenyl group or a $C_3$–$C_4$ alkynyl group.

Between an oxygen atom and an imino group for Y, an oxygen atom is preferred. In the case of Y being an oxygen atom, preferred are the indazoles of the formula (I) wherein Y is an oxygen atom, X is a chlorine atom or a bromine atom, Z is a chlorine atom and R is an isopropyl group, an allyl group, a propargyl group or a 1-methyl-2-propynyl group. In the case of Y being an imino group, preferred are the indazoles of the formula (I) wherein Z is a methyl group and R is a propargyl group. Specifically preferred are 3-chloro-2-(4-chloro-2-fluoro-5-isopropoxyphenyl)-4,5,6,7-tetrahydro-2H-indazole, 3-chloro-2-[4-chloro-2-fluoro-5-(1-propynyloxy)phenyl]-4,5,6,7-tetrahydro-2H-indazole, 3-methyl-2-(4-chloro-2-fluoro-5-propargyloxyphenyl)-4,5,6,7-tetrahydro-2H-indazole, etc.

It is known that certain kinds of indazoles are effective as herbicides. For instance, the herbicidal use of 3-chloro-2-(4-chloro-2-fluorophenyl)-4,5,6,7-tetrahydro-2H-indazole, 3-chloro-2-(2,4-dichloro-5-methoxyphenyl)-4,5,6,7-tetrahydro-2H-indazole, 3-methyl-2-(4-chloro-2-fluorophenyl)-4,5,6,7-tetrahydro-2H-indazole, etc. is disclosed in U.S. Pat. Nos. 4,059,434 and 4,124,374. However, their herbicidal effect is not necessarily satisfactory.

It has now been found that the indazoles (I) show a strong herbicidal activity against a wide variety of weeds including broad-leaved weeds and Graminaceous weeds in agricultural plowed fields as well as weeds in paddy fields at small doses and do not produce any material phytotoxicity on various agricultural crops (i.e. corn, wheat, soybean, cotton, rice plant). Examples of broad-leaved weeds are wild buckwheat (*Polygonum convolvulus*), pale smartweed (*Polygonum lapathifolium*), common purslane (*Portulaca oleracea*), common lambsquarters (*Chenopodium album*), redroot pigweed (*Amaranthus retroflexus*), radish (*Raphanus sativus*), wild mustard (*Brassica kaber*), hemp sesbania (*Sesbania exaltata*), velvetleaf (*Abutilon theophrasti*), prickly sida (*Sida spinosa*), cleavers (*Galium aparine*), ivyleaf morningglory (*Ipomoea hederacea*), tall morningglory (*Ipomoea purpurea*), field bindweed (*Convolvulus arvensis*), jimsonweed (*Datura stramonium*), black nightshade (*Solanum nigrum*), birdseye speedwell (*Veronica persica*), cocklebur (*Xanthium strumarium*), etc. Examples of Graminaceous weeds against which the indazoles (I) exhibit a herbicidal activity are Japanese millet (*Echinochloa frumentacea*), barnyardgrass (*Echinochloa crusgalli*), green foxtail (*Setaria viridis*), large crabgrass (*Digitaria sanguinalis*), annual bluegrass (*Poa annua*), blackgrass (*Alopecurus myosuroides*), oat (*Avena sativa*), wild oat (*Avena fatua*), Johnsongrass (*Sorghum halepense*), quackgrass (*Agropyron repens*), etc. Typical examples of the weeds grown in paddy fields are barnyardgrass (*Echinochloa oryzicola*), monochoria (*Monochoria vaginalis*), arrowhead (*Sagittaria pygmaea*), false pimpernel (*Lindernia pyxidaria*), indian toothcup rotala (*Rotala indica*), bulrush (*Scirpus juncoides*), slender spikerush (*Eleocharis acicularis*), long stemmed waterwort (*Elatine triandra*), etc. The indazoles (I) exert an extremely high herbicidal activity against paddy field weeds without any phytotoxicity to rice plants. Accordingly, the indazoles (I) can be used as herbicides applicable to agricultural plowed fields as well as paddy fields. They are also useful as herbicides to be employed for orchards, pasture lands, forests, non-agricultural fiels, etc.

The indazole (I) is obtainable by reacting a 2,4-dihalo-5-substituted phenyl-4,5,6,7-tetrahydro-2H-indazole of the formula:

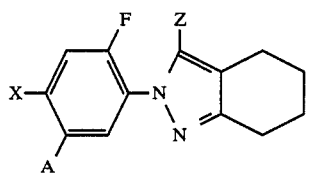

(II)

wherein X and Z are each as defined above and A is an amino group or a hydroxyl group with a halogenated compound of the formula:

(III)

wherein R is as defined above and B is a halogen atom.

The reaction is usually carried out in a solvent in the presence or absence of a base at a temperature of from 0° to 150° C. for a period of 0.5 to 20 hours. The halogenated compound (III) is normally employed in an amount of 1 to 3 equivalents to the starting compound (II). The amount of the base may be ordinarily from 1 to 2 equivalents to the starting compound (II). Examples of the solvent are aromatic hydrocarbons (e.g. benzene, toluene, xylene), halogenated hydrocarbons (e.g., chloroform, carbon tetrachloride, dichloroethane, chlorobenzene, dichlorobenzene), ethers (e.g. diethyl ether, diisopropyl ether, dioxane, tetrahydrofuran, ethylene glycol dimethyl ether), acid amides (e.g. dimethylformamide, dimethylacetamide), water, or their mixtures. As the base, there may be exemplified organic bases (e.g. pyridine, triethylamine, N,N-diethylaniline), inorganic bases (e.g. sodium hydride, sodium hydroxide, potassium hydroxide, sodium carbonate, potassium carbonate), etc.

The thus produced indazole (I) may be subjected to an ordinary post-treatment and, when desired, purified by a per se conventional procedure such as column chromatography or recrystallization.

The indazole (I) wherein Y is an oxygen atom and Z is a chlorine atom is also obtainable by reacting a substituted phenylhydrazine of the formula:

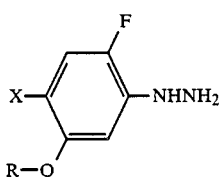
(IV)

wherein X and R are each as defined above with a 2-alkoxycarbonylcyclohexanone of the formula:

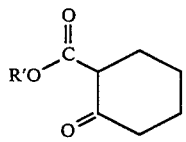
(V)

wherein R' is a $C_1$–$C_4$ alkyl group to give a 2-substituted phenylhexahydroindazol-3-one of the formula:

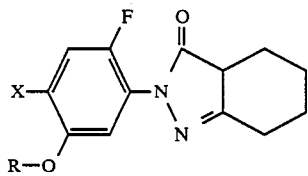
(VI)

wherein X and R are each as defined above, followed by reacting the latter with a chlorinating agent.

The first reaction may be carried out in a solvent at a temperature of 80° C. for a period of 0.5 to 20 hours. The 2-alkoxycarbonylcyclohexanone (V) is usually employed in an amount of 1 to 1.2 equivalents to the substituted phenylhydrazine (IV). Examples of the solvent are toluene, xylene, acetic acid, etc.

The second reaction is normally carried out in a solvent at a temperature of 80° to 200° C. for a period of 5 to 20 hours. The chlorinating agent may be employed in an excessive amount to the intermediary product (VI). Examples of the chlorinating agent are phosphorus oxychloride, thionyl chloride, phosgene, oxalic dichloride, trichloromethyl chloroformate, etc. Examples of the solvent are toluene, xylene, chloroform, etc.

Further, the indazole (I) wherein Y is an oxygen atom and Z is a methyl group can be produced by reacting the substituted phenylhydrazine (IV) with 2-acetylcyclohexanone.

The reaction may be carried out in a solvent in the existence of an acid catalyst at a temperature of 80° to 200° C. for a period of 0.5 to 20 hours. The 2-acetylcyclohexanone is usually employed in an amount of 1 1.2 equivalents to the substituted phenylhydrazine (IV). As the solvent, there may be preferably employed aromatic hydrocarbons such as toluene, xylene, α-methylnaphthalene, and a mixture thereof. Examples of the acid catalyst are inorganic acids (e.g. hydrochloric acid, sulfuric acid), organic acids (e.g. acetic acid, p-toluenesulfonic acid), etc.

The thus produced indazole (I) may be subjected to an ordinary post-treatment and, when desired, purified by a per se conventional procedure such as column chromatography or recrystallization.

Practical and presently preferred embodiments of the production of the objective indazoles (I) are illustratively shown below:

EXAMPLE 1

Into a solution of 3-chloro-2-(4-chloro-2-fluoro-5-hydroxyphenyl)-4,5,6,7-tetrahydro-2H-indazole (0.9 g) in dimethylformamide (10 ml), there were added potassium carbonate (0.25 g) and ethyl iodide (1 g), and the mixture was stirred at 60° C. for 3 hours. After cooling, water was added to the reaction mixture, followed by extraction with ether. The ether layer was washed with water twice, dried and concentrated. The residue was crystallized from hexane to give 0.2 g of 3-chloro-2-(4-chloro-2-fluoro-5-ethoxyphenyl-4,5,6,7-tetrahydro-2H-indazole (Compound No. 1). m.p., 85.1° C.

EXAMPLE 2

A mixture of 2-(4-chloro-2-fluoro-5-isopropoxyphenyl)-1,2,4,5,6,7-hexahydro-3H-indazol-3-one (1 g) and phosphorus oxychloride (0.7 g) was heated under reflux heating for 6 hours. After cooling, the reaction mixture was dissolved in chloroform, washed with a 5% sodium hydroxide solution and water, dried and concentrated. The residue was purified by silica gel column chromatography to give 0.3 g of 3-chloro-2-(4-chloro-2-fluoro-5-isopropoxyphenyl)-4,5,6,7-tetrahydro-2H-indazole (Compound No. 2). $n_D^{26}$ 1.5530.

EXAMPLE 3

4-Chloro-2-fluoro-5-isopropoxyphenylhydrazine (1.8 g), 2-acetylcyclohexanone (1.0 g) and a catalytic amount of acetic acid were dissolved in xylene (5 ml). The resultant mixture was heated under reflux for 8 hours while removing water. After cooling, the reaction mixture was concentrated under reduced pressure, and the residue was purified by silica gel column chromatography to give 0.9 g of 3-methyl-2-(4-chloro-2-fluoro-5-isopropoxyphenyl)-4,5,6,7-tetrahydro-2H-indazole (Compound No. 5). $n_D^{14.5}$ 1.5607.

Examples of the indazole (I) produced in the same manner as above are shown in Table 1.

TABLE 1 (I)

| Compound No. | X | Y | Z | R | Physical property |
|---|---|---|---|---|---|
| 1 | Cl | O | Cl | —CH$_2$CH$_3$ | m.p. 85.1° C. |
| 2 | Cl | O | Cl | —CH$_2$(CH$_3$)$_2$ | $n_D^{26}$ 1.5530 |
| 3 | Cl | O | Cl | —(CH$_2$)$_3$CH$_3$ | $n_D^{28}$ 1.5492 |
| 4 | Cl | O | CH$_3$ | —CH$_2$CH$_3$ | m.p. 98–99° C. |
| 5 | Cl | O | CH$_3$ | —CH$_2$(CH$_3$)$_2$ | $n_D^{14.5}$ 1.5607 |
| 6 | Cl | O | Cl | —CH$_2$CH=CH$_2$ | m.p. 91.3° C. |
| 7 | Cl | O | Cl | —CH(CH$_3$)—CH=CH$_2$ | $n_D^{25}$ 1.5670 |

TABLE 1-continued

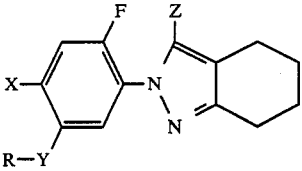

| Compound No. | X | Y | Z | R | Physical property |
|---|---|---|---|---|---|
| 8 | Cl | O | Cl | —CH₂CH=CHCH₃ | m.p. 77–78° C. |
| 9 | Cl | O | Cl | —CH₂—C(CH₃)=CH₂ | m.p. 52–53.5° C. |
| 10 | Cl | O | Cl | —CH₂C≡CH | m.p. 116–117° C. |
| 11 | Cl | O | Cl | —CH(CH₃)—C≡CH | $n_D^{20.7}$ 1.5535 |
| 12 | Cl | O | CH₃ | —CH₂CHCH₂ | m.p. 128° C. |
| 13 | Cl | O | CH₃ | —CH₂C≡CH | m.p. 143–144° C. |
| 14 | Cl | —NH | CH₃ | —CH₂C≡CH | m.p. 117.7° C. |
| 15 | Br | O | Cl | —CH(CH₃)₂ | $n_D^{22}$ 1.5734 |
| 16 | Br | O | Cl | —CH₂CH=CH₂ | m.p. 101.9° C. |
| 17 | Br | O | Cl | —CH₂C≡CH | m.p. 121.2° C. |
| 18 | Br | O | CH₃ | —CH(CH₃)₂ | $n_D^{19.5}$ 1.5732 |

The starting 2,4-dihalo-5-substituted phenyl-4,5,6,7-tetrahydro-2H-indazole (II) wherein A is a hydroxyl group and Z is a chlorine atom is obtainable by reacting a 2,4-dihalo-5-hydroxyphenylhydrazine of the formula:

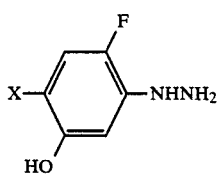
(VII)

wherein X is as defined above with the 2-alkoxycarbonylcyclohexanone (V) in the same manner as in the reaction between the compound (IV) and the compound (V) to produce a 2-(2,4-dihalo-5-hydroxyphenyl)hexahydroindazol-3-one of the formula:

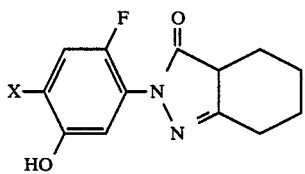
(VIII)

wherein X is as defined above, followed by reacting the latter with a chlorinating agent in the same manner as in the reaction between the compound (VI) and the chlorinating agent.

The 2,4-dihalo-5-substituted phenyl-4,5,6,7-tetrahydro-2H-indazole (II) wherein A is a hydroxyl group and Z is a methyl group may be also produced by reacting the 2,4-dihalo-5-hydroxyphenylhydrazine (VII) with 2-acetylcyclohexanone in the same manner as in the reaction between the compound (IV) and 2-acetylcyclohexanone.

The 2,4-dihalo-5-substituted phenyl-4,5,6,7-tetrahydro-2H-indazole (II) wherein A is an amino group is obtainable by reacting a 2,4-dihalo-5-nitrophenylhydrazine of the formula:

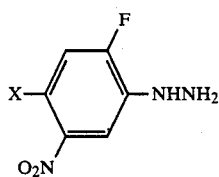
(IX)

wherein X is as defined above with the 2-alkoxycarbonylcyclohexanone (V) as in the reaction between the compound (IV) and the compound (V) to give a 2-(2,4-dihalo-5-nitrophenyl)hexahydroindazol-3-one of the formula:

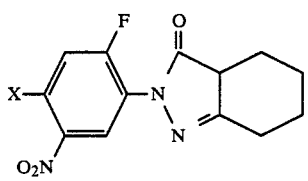
(X)

wherein X is as defined above, followed by reacting the latter with a chlorinating agent as in the reaction between the compound (VI) and the chlorinating agent, or by reacting the 2,4-dihalo-5-nitrophenylhydrazine (IX) with 2-acetylcyclohexanone as in the reaction between the compound (IV) and 2-acetylcyclohexanone to give a 2,4-dihalo-5-nitrophenyl-4,5,6,7-tetrahydro-2H-indazole of the formula:

(XI)

wherein X and Z are as defined above, followed by subjecting the latter to reduction by a per se conventional procedure such as reduction with an acid (e.g. hydrochloric acid, acetic acid) and iron powder.

The intermediary phenylhydrazine compounds, i.e. the substituted phenylhydrazine (IV), the 2,4-dihalo-5-hydroxyphenylhydrazine (VII) and the 2,4-dihalo-5-nitrophenylhydrazine (IX), may be produced according to the following scheme:

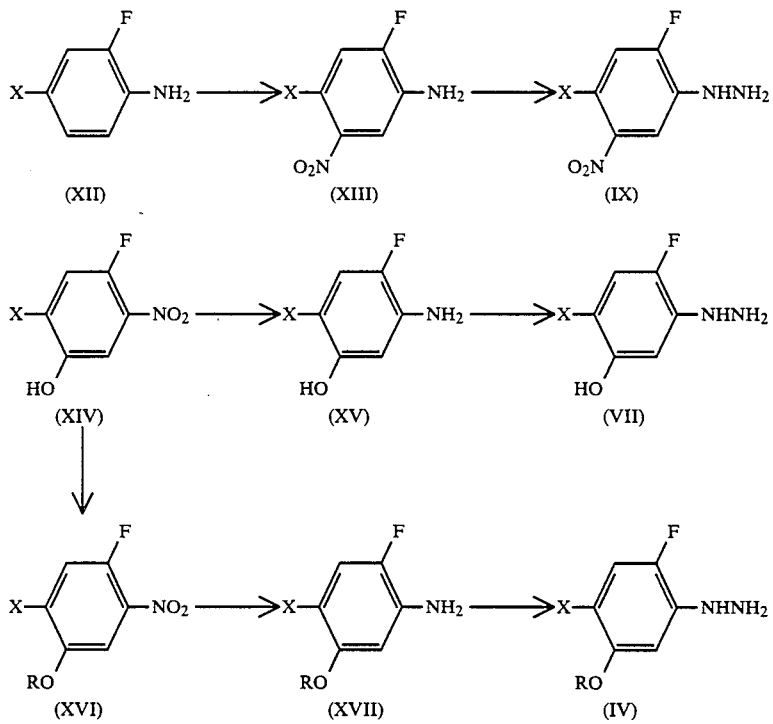

wherein X and R are each as defined above.

The above conversions are known and described, for instance, in U.S. Pat. No. 4,124,374, EP-0061741A, EP-0083055A and J.Chem.Soc., Commun., 2106 (1970).

Typical examples for the production of the starting compounds are illustratively shown below:

EXAMPLE 4

Production of the 2,4-dihalo-5-substituted phenyl-4,5,6,7-tetrahydro-2H-indazole (II: X=Z=Cl; A=OH)

A solution of 2-fluoro-4-chloro-5-hydroxyphenylhydrazine (8 g) and 2-ethoxycarbonylcyclohexanone (8 g) in acetic acid (30 ml) was heated under reflux for 4 hours. After cooling, the precipitated crystals were collected by filtration and washed with ether to give 11 g of 2-(4-chloro-2-fluoro-5-hydroxyphenyl)-2,3a,4,5,6,7-hexahydroindazol-3-one. m.p., 273°–275° C. (decomp.).

The product thus obtained was added to a 1M solution of phosgene in toluene (400 ml), and the resultant mixture was heated under reflux for 3 hours. After cooling, the mixture was concentrated, and the residue was purified by silica gel column chromatography to obtain 3 g of 3-chloro-2-(4-chloro-2-fluoro-5-hydroxyphenyl)-4,5,6,7-tetrahydro-2H-indazole. m.p., 183°–185° C.

EXAMPLE 5

Production of the 2,4-dihalo-5-substituted phenyl-4,5,6,7-tetrahydro-2H-indazole (II; X=Br; Z=Cl; A=OH)

In the same manner as in Example 4 but using 4-bromo-2-fluoro-5-hydroxyphenylhydrazine, there was obtained 3-chloro-2-(4-bromo-2-fluoro-5-hydroxyphenyl)-4,5,6,7-tetrahydro-2H-indazole. m.p., 174.3° C.

EXAMPLE 6

Production of the 2,4-dihalo-5-substituted phenyl-4,5,6,7-tetrahydro-2H-indazole (II: X=Cl, Z=CH₃; A=OH)

4-Chloro-2-fluoro-5-hydroxyphenylhydrazine (0.5 g), 2-acetylcyclohexanone (0.4 g) and a catalytic amount of acetic acid were admixed with xylene (15 ml), and the resultant mixture was heated under reflux for 5 hours while removing water. After cooling, the mixture was concentrated, and the residue was purified by silica gel column chromatography to obtain 0.7 g of 2-(4-chloro-2-fluoro-5-hydroxyphenyl)-3-methyl-4,5,6,7-tetrahydro-2H-indazole. m.p., 188.5°–190° C.

EXAMPLE 7

Production of the 2,4-dihalo-5-substituted phenyl-4,5,6,7-tetrahydro-2H-indazole (II: X=Cl; Z=CH₃; A=NH₂)

A mixture of iron powder (3 g) and a 5% aqueous acetic acid solution (10 ml) was heated at 90° to 100° C. while stirring for 10 minutes. To the resulting mixture, there was dropwise added 2-(4-chloro-2-fluoro-5-nitrophenyl)-3-methyl-4,5,6,7-tetrahydro-2H-indazole (2 g) in acetic acid (10 ml) and ethyl acetate (10 ml), followed by stirring at the same temperature for 1 hour. After cooling, the iron powder was eliminated by filtration, and the filtrate was extracted with ethyl acetate. The organic layer was washed with a saturated sodium bicarbonate solution, dried and concentrated. The crystallized residue was collected by filtration and washed with ether to obtain 1.8 g of 2-(4-chloro-2-fluoro-5-aminophenyl)-3-methyl-4,5,6,7-tetrahydro-2H-indazole. m.p., 107°–108° C.

Some examples of the 2,4-dihalo-5-substituted phenyl-4,5,6,7-tetrahydro-2H-indazole (II) wherein A is an amino group produced in the same manner as in Example 7 are shown in Table 2.

TABLE 2

(II) Structure: fluorine and Z substituted indazole-type with X and H₂N on phenyl ring fused to cyclohexane via N-N.

| X | Z | Physical property |
|---|---|---|
| Br | Cl | Glassy |
| Br | CH₃ | m.p. 69-71° C. |

EXAMPLE 8

Production of the substituted phenylhydrazine (VII)

4-Chloro-2-fluoro-5-hydroxyaniline (10 g) was dissolved in conc. hydrochloric acid (130 ml) under heating, and the resultant mixture was cooled to 0° C. To the resulting mixture, there was dropwise added a solution of sodium nitrite (4.5 g) in water (20 ml). After completion of the addition, the mixture was further stirred at 5° to −5° C. for 1 hour, and urea was added thereto, whereby excessive sodium nitrite ion was decomposed. The resulting mixture was cooled to −30° to −25° C., and a solution of anhydrous stannous chloride (20.5 g) in conc. hydrochloric acid (40 ml) was added thereto, followed by stirring at −10° to 0° C. for 3 hours. The precipitated crystals were collected by filtration, washed with a small amount of water and dissolved in a 10% aqueous sodium hydroxide solution. The resultant solution was adjusted to pH 7 and extracted with ethyl acetate. The extract was dried and concentrated. The crystallized residue was washed with ether to obtain 1 g of 4-chloro-2-fluoro-5-hydroxyphenylhydrazine. m.p. 149°-150° C. (decomp.).

Some examples of the substituted phenylhydrazines (IX) and (IV) produced in the same manner as in Example 8 are shown in Tables 3A and 3B.

TABLE 3A (IX) Structure: phenyl ring with F, X, NHNH₂, and O₂N substituents.

| X | Physical property |
|---|---|
| Cl | m.p. 116-117° C. |
| Br | m.p. 110-111° C. |

TABLE 3B (IV) Structure: phenyl ring with F, X, NHNH₂, and R—O substituents.

| X | R | Physical property |
|---|---|---|
| Cl | —CH(CH₃)₂ | m.p. 67-68° C. |
| Cl | —CH₂C≡CH | m.p. 67-67.5° C. |

TABLE 3B-continued (IV) Structure: phenyl ring with F, X, NHNH₂, and R—O substituents.

| X | R | Physical property |
|---|---|---|
| Br | —CH(CH₃)₂ | m.p. 65-65.5° C. |

EXAMPLE 9

Production of the 2,4-dihalo-5-nitrophenyl-4,5,6,7-tetrahydro-2H-indazole (XI)

In the same manner as in Example 6 but using 4-chloro-2-fluoro-5-nitrophenylhydrazine (4 g), 2-acetylcyclohexanone (2.8 g), a catalytic amount of acetic acid and xylene (10 ml), there was produced 2.3 g of 2-(4-chloro-2-fluoro-5-nitrophenyl)-3-methyl-4,5,6,7-tetrahydro-2H-indazole. m.p., 143°-144° C.

EXAMPLE 10

Production of the 2,4-dihalo-5-nitrophenyl-4,5,6,7-tetrahydro-2H-indazole (XI)

In the same manner as in Example 5 but using a solution of 4-chloro-2-fluoro-5-nitrophenylhydrazine (4.6 g), 2-ethoxycarbonylcyclohexanone (3.9 g) in acetic acid (20 ml), there was prepared 2-(4-chloro-2-fluoro-5-nitrophenyl)-2,3a,4,5,6,7-hexahydroindazol-3-one (4.2 g).

The thus obtained product was treated with a 1M solution of phosgene in toluene (300 ml) in the same manner as in Example 5 to obtain 0.8 g of 3-chloro-2-(4-chloro-2-fluoro-5-nitrophenyl)-4,5,6,7-tetrahydro-2H-indazole. m.p., 120°-122° C.

EXAMPLE 11

Production of the nitroaniline (XIII)

4-Chloro-2-fluoroaniline (23 g) was dissolved in conc. sulfuric acid (120 ml), and the resultant mixture was cooled to −20° C., followed by dropwise addition of fuming nitric acid (15 g). The reaction mixture was stirred at −20° to −15° C. for 1.5 hours, poured into ice-water and then extracted with ether. The ether extract was washed with water and a saturated sodium bicarbonate solution, dried and concentrated. The residue was crystallized from a mixture of toluene and hexane (2:1) to obtain 20 g of 4-chloro-2-fluoro-5-nitroaniline. m.p., 83°-84.5° C.

EXAMPLE 12

In the same manner as in Example 11 but using 4-bromo-2-fluoroaniline, there was obtained 4-bromo-2-fluoro-5-nitroaniline. m.p., 90°-92° C.

In the practical use of the indazoles (I), they may be applied in any preparation form such as emulsifiable concentrates, wettable powders, suspensions, granules, etc. in combination with a conventional solid or liquid carrier or diluent, a surface active agent or an auxiliary agent.

The content of the indazole (I) as the active ingredient in such preparation forms is usually within a range of 0.03 to 80% by weight, preferably of 0.07 to 70% by weight.

Examples of the solid carrier or diluent are kaolin clay, attapulgite clay, bentonite, terra alba, pyrophyllite, talc, diatomaceous earth, calcite, walnut powders, urea, ammonium sulfate, synthetic hydrous silicate, etc. As the liquid carrier or diluent, there may be exemplified aromatic hydrocarbons (e.g., xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, acetonitrile, water, etc.

The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts and % are by weight. The compound number of the active ingredient corresponds to the one in Table 1.

PREPARATION EXAMPLE 1

Fifty parts of Compound No. 1, 8 or 13, 3 parts of calcium ligninsulfonate, 2 parts of sodium laurylsulfate and 45 parts of synthetic hydrous silicate are well mixed while being powdered to obtain a wettable powder.

PREPARATION EXAMPLE 2

Ten parts of Compound No. 2, 3 or 10, 14 parts of polyoxyethylenestyrylphenyl ether, 6 parts of calcium dodecylbenzenesulfonate and 70 parts of cyclohexanone are well mixed while being powdered to obtain an emulsifiable concentrate.

PREPARATION EXAMPLE 3

Two parts of Compound No. 2 or 10, 1 part of synthetic hydrous silicate, 2 parts of calcium lignin-sulfonate, 30 parts of bentonite and 65 parts of kaolin clay are well mixed while being powdered. The mixture is then kneaded with water, granulated and dried to obtain granules.

PREPARATION EXAMPLE 4

Twenty-five parts of Compound No. 1, 2 or 8 is mixed with 3 parts of polyoxyethylene sorbitan monooleate, 3 parts of carboxymethyl cellulose and 69 parts of water and pulverized until the particle size of the active ingredient becomes less than 5 microns to obtain a suspension.

PREPARATION EXAMPLE 5

0.07 Part of Compound No. 10 or 13, 1 part of synthetic hydrous silicate, 4 parts of sodium dodecylbenzenesulfonate, 30 parts of bentonite and 64.93 parts of kaolin clay are well mixed while being powdered. The mixture is then kneaded with water, granulated and dried to obtain granules.

The indazoles (I) thus formulated in any suitable preparation form are useful for the pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the indazoles (I) over the top of the plants. It may also be applied directly to the weeds if care is taken to keep the chemical off the crop foliage.

The indazoles (I) of the invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

The dosage rate of the indazoles (I) may vary on prevailing weather conditions, preparation used, prevailing season, mode of application, soil involved, crop and weed species, etc. Generally, however, the dosage rate is from 0.01 to 40 grams, preferably from 0.05 to 30 grams, of the active ingredient per are. The herbicidal composition of the invention prepared in the form of an emulsifiable concentrate, a wettable powder or a suspension may ordinarily be employed by diluting it with water at a volume of 1 to 10 liters per are, if necessary, with addition the of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition prepared in the form of granules may be normally applied as such without dilution.

The biological data of the indazoles (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates that no material difference is seen in comparison with the untreated plant and the numeral "5" indicates the complete inhibition or death of the test plants.

The compounds shown in Table 4 below were used for comparison.

TABLE 4

| Compound No. | Chemical structure | Remarks |
| --- | --- | --- |
| A | 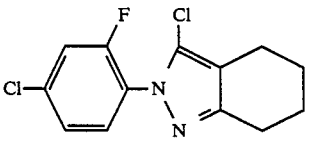 | U.S. Pat. No. 4,059,434 |

TABLE 4-continued

| Compound No. | Chemical structure | Remarks |
|---|---|---|
| B | 2-fluoro-5-isopropoxyphenyl group attached to N of 3-chloro-4,5,6,7-tetrahydro-2H-indazole | Synthesized for comparison $n_D^{25.5}$ 1.5551 |
| C | 2,4-dichloro-5-methoxyphenyl group attached to N of 3-chloro-4,5,6,7-tetrahydro-2H-indazole | U.S. Pat. No. 4,059,434 |
| D | 4-chloro-2-fluorophenyl group attached to N of 3-methyl-4,5,6,7-tetrahydro-2H-indazole | U.S. Pat. No. 4,124,374 |
| E | 2,4-dichloro-5-isopropoxyphenyl group attached to N of 3-methyl-4,5,6,7-tetrahydro-2H-indazole | U.S. Pat. No. 4,124,374 |
| F | 2,4-dichlorophenyl-O-(3-methoxy-4-nitrophenyl) | Commercially available herbicide; "Chlomethoxynil" |
| G | 2-chloro-4-trifluoromethylphenyl-O-(2-carboxy-4-nitrophenyl) sodium salt | Commercially available herbicide; "acifluorufen" |
| H | 2-chloro-4-trifluoromethylphenyl-O-(3-ethoxy-4-nitrophenyl) | Commercially available herbicide; "oxyfluorfen" |

TEST EXAMPLE 1

Vats (33 cm × 23 cm × 11 cm) were filled with upland field soil and the seeds of corn, wheat, soybean, cotton, oat (*Avena sativa*), barnyardgrass (*Echinochloa crusgalli*), large crabgrass, green foxtail, hemp sesbania, cocklebur, velvetleaf, tall morningglory, redroot pigweed and black nightshade were sowed therein. Cultivation was carried out in a greenhouse for 18 days. A designated amount of the test compound formulated into an emulsifiable concentrate according to Preparation Example 2 and diluted with water containing a spreading agent was sprayed to the foliage of the test plants over the top by means of a small hand sprayer at a spray volume of 5 liters per are. Thereafter, the test plants were further grown in the greenhouse for 20 days, and the herbicidal activity and the phytotoxicity were examined. At the time of the application, the growing stage of the test plants varied depending on their species but, they were generally at the 1 to 4 leaf stage and in 2 to 12 cm height. The results are shown in Table 5.

TABLE 5

| Compound No. | Dosage (g/are) | Phytotoxicity | | | | Herbicidal activity | | | | | | | | | |
|---|---|---|---|---|---|---|---|---|---|---|---|---|---|---|---|
| | | Corn | Wheat | Soybean | Cotton | Oat | Barnyardgrass | Large crabgrass | Green foxtail | Hemp sesbania | Cocklebur | Velvetleaf | Tall morningglory | Redroot pigweed | Black nightshade |
| 2 | 0.32 | 1 | 1 | 4 | 3 | 1 | 5 | 4 | 3 | 5 | 5 | 5 | 5 | 5 | 5 |
| | 0.16 | 1 | 0 | 3 | 2 | 0 | 4 | 3 | 2 | 5 | 5 | 5 | 4 | 4 | 4 |

TABLE 5-continued

| Compound No. | Dosage (g/are) | Phytotoxicity | | | | Herbicidal activity | | | | | | | | | |
|---|---|---|---|---|---|---|---|---|---|---|---|---|---|---|---|
| | | Corn | Wheat | Soybean | Cotton | Oat | Barnyardgrass | Large crabgrass | Green foxtail | Hemp sesbania | Cocklebur | Velvetleaf | Tall morningglory | Redroot pigweed | Black nightshade |
| | 0.08 | 0 | 0 | 2 | 1 | 0 | 3 | 0 | 1 | 5 | 5 | 5 | 3 | 3 | 2 |
| 3 | 0.32 | 1 | 1 | 3 | 4 | 3 | 5 | 4 | 4 | 5 | 5 | 5 | 5 | 5 | 5 |
| | 0.16 | 0 | 0 | 2 | 2 | 1 | 4 | 3 | 2 | 5 | 5 | 5 | 4 | 4 | 4 |
| | 0.08 | 0 | 0 | 1 | 1 | 0 | 3 | 2 | 1 | 4 | 4 | 5 | 3 | 3 | 3 |
| 5 | 0.32 | 0 | 0 | — | — | — | 4 | — | — | 5 | 5 | 5 | 5 | 5 | 5 |
| | 0.16 | 0 | 0 | 2 | — | — | 3 | — | — | 5 | 4 | 5 | 4 | 5 | 5 |
| 9 | 0.32 | 3 | 1 | — | 5 | — | 5 | — | — | 5 | 5 | 5 | 5 | 5 | 5 |
| | 0.16 | 1 | 0 | — | 3 | — | 4 | — | — | 5 | 5 | 5 | 4 | 5 | 5 |
| 10 | 0.32 | 3 | 2 | 4 | 5 | 4 | 5 | 5 | 5 | 5 | 5 | 5 | 5 | 5 | 5 |
| | 0.16 | 1 | 1 | 3 | 5 | 3 | 5 | 4 | 5 | 5 | 5 | 5 | 5 | 5 | 5 |
| | 0.08 | 1 | 0 | 2 | 5 | 2 | 4 | 3 | 3 | 5 | 5 | 5 | 5 | 5 | 5 |
| 11 | 0.32 | 3 | 1 | — | 5 | — | 5 | — | — | 5 | 5 | 5 | 5 | 5 | 5 |
| | 0.16 | 1 | 0 | — | 4 | — | 4 | — | — | 5 | 5 | 5 | 5 | 5 | 5 |
| 13 | 0.32 | — | 1 | — | — | — | 5 | — | — | 5 | 5 | 5 | 5 | 5 | 5 |
| | 0.16 | — | 1 | — | — | — | 4 | — | — | 5 | 5 | 5 | 5 | 5 | 5 |
| 14 | 0.32 | 3 | 1 | — | — | — | 4 | — | — | 5 | 4 | 5 | 5 | 5 | 5 |
| | 0.16 | 1 | 0 | — | — | — | 3 | — | — | 5 | 4 | 5 | 4 | 5 | 5 |
| A | 0.32 | 1 | 0 | 3 | 3 | 0 | 1 | 0 | 0 | 4 | 3 | 4 | 2 | 1 | 3 |
| | 0.16 | 1 | 0 | 2 | 2 | 0 | 0 | 0 | 0 | 2 | 2 | 3 | 0 | 1 | 2 |
| | 0.08 | 0 | 0 | 1 | 1 | 0 | 0 | 0 | 0 | 1 | 1 | 1 | 0 | 0 | 1 |
| B | 0.32 | 0 | 0 | 2 | 3 | 0 | 0 | 0 | 0 | 3 | 2 | 4 | 1 | 2 | 3 |
| | 0.16 | 0 | 0 | 1 | 1 | 0 | 0 | 0 | 0 | 2 | 0 | 3 | 0 | 0 | 1 |
| D | 5.0 | 2 | 2 | 3 | — | — | — | — | — | 4 | 4 | 5 | 5 | 5 | — |
| | 1.25 | 1 | 1 | 3 | — | — | — | — | — | 3 | 3 | 5 | 2 | 5 | — |
| | 0.32 | 1 | 1 | 3 | — | — | — | — | — | 2 | 1 | 3 | 1 | 3 | — |
| G | 1.25 | 1 | 1 | 2 | 4 | 2 | 1 | 2 | 2 | 5 | 3 | 3 | 4 | 5 | 4 |
| | 0.32 | 0 | 0 | 1 | 2 | 0 | 0 | 1 | 0 | 3 | 1 | 1 | 2 | 3 | 2 |

TEST EXAMPLE 2

Wagner's pots (1/5000 are) were filled with paddy field soil, and the seeds of barnyardgrass (*Echinochloa cryzicola*), broad-leaved weeds (e.g. false pimpernel, toothcup, waterwort) and hardstem bulrush and the buds of slender spikerush were sowed in 1 to 2 cm depth. Water was poured therein to make a flooded condition. Rice seedlings of the 3-leaf stage were transplanted therein and grown in a greenhouse. Four days (at that time barnyardgrass started to germinate) thereafter, a designated amount of the test compound formulated in an emulsifiable concentrate according to Preparation Example 2 and diluted with water (10 ml) was applied to the pots by perfusion. The test plants were grown for further 20 days in the greenhouse, and the herbicidal activity and the phytotoxicity were examined. The results are shown in Table 6.

TABLE 6

| Compound No. | Dosage (g/are) | Phytotoxicity Rice plant | Herbicidal activity | | | |
|---|---|---|---|---|---|---|
| | | | Barnyardgrass | Broad-leaved weed | Slender spikerush | Hardstem bulrush |
| 1 | 0.32 | 1 | 5 | 5 | 5 | 5 |
| | 0.16 | 1 | 5 | 5 | 5 | 4 |
| | 0.08 | 0 | 5 | 5 | 4 | 2 |
| 2 | 0.32 | 1 | 5 | 5 | 5 | 5 |
| | 0.16 | 1 | 5 | 5 | 5 | 4 |
| | 0.08 | 0 | 5 | 5 | 4 | 2 |
| 3 | 0.32 | 1 | 5 | 5 | 5 | 4 |
| | 0.16 | 1 | 5 | 5 | 4 | 2 |
| | 0.08 | 0 | 4 | 5 | 3 | 1 |
| 5 | 0.32 | 0 | 5 | 5 | 5 | 4 |
| | 0.16 | 0 | 4 | 5 | 4 | 4 |
| 6 | 0.32 | 1 | 5 | 5 | 5 | 5 |
| 7 | 0.32 | 1 | 5 | 5 | 5 | 5 |
| 8 | 0.32 | 1 | 5 | 5 | 5 | 5 |
| 9 | 0.32 | 1 | 5 | 5 | 5 | 4 |
| 10 | 0.16 | 1 | 5 | 5 | 5 | 5 |
| | 0.08 | 1 | 5 | 5 | 5 | 4 |
| | 0.04 | 0 | 5 | 5 | 4 | 3 |
| 11 | 0.32 | 1 | 5 | 5 | 5 | 5 |
| | 0.16 | 1 | 5 | 5 | 5 | 5 |
| 13 | 0.32 | 1 | 5 | 5 | 5 | 4 |
| | 0.16 | 1 | 5 | 5 | 5 | 4 |
| 14 | 0.32 | 1 | 5 | 5 | 5 | 4 |
| | 0.16 | 1 | 5 | 5 | 4 | 4 |
| A | 0.32 | 1 | 4 | 5 | 4 | 4 |
| | 0.16 | 1 | 3 | 5 | 3 | 4 |
| | 0.08 | 0 | 2 | 5 | 2 | 2 |
| B | 0.32 | 1 | 3 | 5 | 3 | 3 |
| | 0.16 | 1 | 2 | 5 | 1 | 2 |
| | 0.08 | 0 | 1 | 5 | 0 | 0 |

TABLE 6-continued

| Compound No. | Dosage (g/are) | Phytotoxicity Rice plant | Herbicidal activity Barnyardgrass | Broad-leaved weed | Slender spikerush | Hardstem bulrush |
|---|---|---|---|---|---|---|
| C | 0.32 | 2 | 3 | 5 | 3 | 2 |
|   | 0.16 | 0 | 1 | 4 | 2 | 0 |
|   | 0.08 | 0 | 0 | 2 | 0 | 0 |
| F | 1.25 | 1 | 4 | 5 | 5 | 4 |
|   | 0.32 | 0 | 2 | 5 | 2 | 2 |

TEST EXAMPLE 3

Cylindrical plastic pots (diameter, 10 cm; length, 10 cm) were filled with upland field soil, and the seeds of barnyardgrass, velvetleaf, tall morningglory and redroot pigweed were sowed therein. A designated amount of the test compound formulated into an emulsifiable concentrate and diluted with water was sprayed to the soil surface over the top by means of a small hand sprayer at a spray volume of 10 liters per are and the soil was admixed well to the depth of 4 cm. Cultivation was carried out in a greenhouse for 20 days, and the herbicidal activity and the phytotoxicity were examined. The results are shown in Table 7.

TABLE 7

| Compound No. | Dosage (g/are) | Herbicidal activity Barnyardgrass | Velvetleaf | Tall morningglory | Redroot pigweed |
|---|---|---|---|---|---|
| 1 | 40 | 5 | 5 | 5 | 5 |
|   | 20 | 5 | 5 | 5 | 5 |
|   | 10 | 4 | 5 | 4 | 5 |
| 2 | 40 | 5 | 5 | 5 | 5 |
|   | 20 | 5 | 5 | 5 | 5 |
|   | 10 | 5 | 5 | 4 | 5 |
| 3 | 40 | 5 | 5 | 5 | 5 |
|   | 20 | 5 | 5 | 4 | 5 |
|   | 10 | 4 | 5 | 3 | 5 |
| 4 | 20 | 5 | 5 | 5 | 5 |
|   | 10 | 5 | 5 | 3 | 5 |
| 5 | 20 | 5 | 5 | 5 | 5 |
|   | 10 | 5 | 5 | 3 | 5 |
| 6 | 20 | 5 | 5 | 5 | 5 |
|   | 10 | 5 | 5 | 4 | 5 |
| 7 | 20 | 5 | 5 | 5 | 5 |
|   | 10 | 5 | 5 | 4 | 5 |
| 8 | 20 | 5 | 5 | 5 | 5 |
|   | 10 | 5 | 5 | 4 | 5 |
| 9 | 20 | 5 | 5 | 5 | 5 |
|   | 10 | 5 | 5 | 4 | 5 |
| 10 | 20 | 5 | 5 | 5 | 5 |
|   | 10 | 5 | 5 | 5 | 5 |
|   | 5 | 5 | 5 | 4 | 5 |
| 11 | 40 | 5 | 5 | 5 | 5 |
| 12 | 20 | 5 | 5 | 5 | 5 |
|   | 10 | 5 | 5 | 3 | 5 |
| 13 | 20 | 5 | 5 | 5 | 5 |
|   | 10 | 5 | 5 | 4 | 5 |
| 14 | 20 | 4 | 5 | 5 | 5 |
|   | 10 | 4 | 5 | 3 | 5 |
| 15 | 40 | 5 | 5 | 5 | 5 |
|   | 20 | 5 | 5 | 5 | 5 |
| 16 | 40 | 5 | 5 | 5 | 5 |
|   | 20 | 5 | 5 | 5 | 5 |
| 17 | 40 | 5 | 5 | 5 | 5 |
|   | 20 | 5 | 5 | 5 | 5 |
| A | 40 | 5 | 5 | 3 | 5 |
|   | 20 | 5 | 5 | 2 | 5 |
|   | 10 | 5 | 3 | 1 | 5 |
| B | 40 | 5 | 4 | 3 | 5 |
|   | 20 | 4 | 3 | 2 | 4 |
| C | 40 | 4 | 4 | 2 | 4 |
|   | 20 | 2 | 3 | 2 | 4 |
| E | 40 | 3 | 4 | 1 | 4 |
|   | 20 | 1 | 1 | 1 | 3 |

TEST EXAMPLE 4

Vats (33 cm×23 cm×11 cm) were filled with upland field soil, and the seeds of soybean, cocklebur, tall morningglory, velvetleaf, black nightshade, jimsonweed, green foxtail and barnyardgrass (*Echinochloa crus-galli*) were sowed therein at the depth of 1 to 2 cm. A designated amount of the test compound formulated into an emulsifiable concentrate according to Preparation Example 2 and diluted with water was sprayed to the soil surface over the top by means of a small hand sprayer at a spray volume of 10 liters per are. Thereafter, cultivation was carried out in outdoors for 20 days, and the herbicidal activity and the phytotoxicity were examined. The results are shown in Table 8.

TABLE 8

| Compound No. | Dosage (g/are) | Phytotoxicity Soybean | Herbicidal activity Cocklebur | Tall morningglory | Velvetleaf | Black nightshade | Jimsonweed | Green foxtail | Barnyardgrass |
|---|---|---|---|---|---|---|---|---|---|
| 1 | 2.5 | 1 | 5 | 5 | 5 | 5 | 5 | 5 | 5 |
|   | 1.25 | 0 | 4 | 5 | 5 | 5 | 5 | 5 | 5 |
| 2 | 2.5 | 1 | 5 | 5 | 5 | 5 | 5 | 5 | 5 |
|   | 1.25 | 0 | 4 | 5 | 5 | 5 | 5 | 5 | 5 |
| 5 | 5 | 0 | — | 5 | 5 | 5 | — | 5 | 5 |
|   | 2.5 | 0 | — | 4 | 5 | 5 | — | 4 | 3 |
| 9 | 5 | 1 | 5 | 5 | 5 | 5 | 5 | 5 | 5 |
|   | 2.5 | 0 | 4 | 4 | 5 | 5 | 5 | 5 | 5 |
| 10 | 2.5 | 1 | 5 | 5 | 5 | 5 | 5 | 5 | 5 |
|   | 1.25 | 1 | 5 | 5 | 5 | 5 | 5 | 5 | 5 |
| 11 | 5 | 1 | 5 | 5 | 5 | 5 | 5 | 5 | 5 |
|   | 2.5 | 0 | 4 | 5 | 5 | 5 | 5 | 5 | 5 |
| 13 | 5 | — | 5 | 5 | 5 | 5 | — | 5 | 5 |
|   | 2.5 | 1 | — | 4 | 5 | 5 | — | 5 | 4 |

TABLE 8-continued

| Compound No. | Dosage (g/are) | Phytotoxicity Soybean | Herbicidal activity | | | | | | |
|---|---|---|---|---|---|---|---|---|---|
| | | | Cocklebur | Tall morning-glory | Velvetleaf | Black nightshade | Jimsonweed | Green foxtail | Barnyardgrass |
| G | 2.5 | 3 | 3 | 4 | 4 | 5 | 5 | 3 | 3 |
| | 1.25 | 0 | 1 | 1 | 3 | 4 | 4 | 1 | 0 |

TEST EXAMPLE 5

Concrete pots (50×50 cm) were filled with paddy field soil, and the seeds of barnyardgrass, broad-leaved weeds (e.g. common falsepimpernel, indian toothcup, waterwort) and monochoria and the statoblasts of needle spikerush were sowed in 1 to 2 cm depth. Water was poured therein to make a flooded condition. Rice seedlings of the 3-leaf stage were transplanted therein and grown in outdoors. Four days thereafter, a designated amount of the test compound formulated in granules according to Preparation Example 5 was applied to the pots with two replications. The test plants were grown for further 40 days in outdoors, and the growth inhibition percentage was determined by weighing the fresh weight of the test plants and calculated according to the following equation:

$$\text{Growth inhibition percentage (\%)} = \left\{ 1 - \frac{\text{Fresh weight of test plants in treated plot}}{\text{Fresh weight of test plants in untreated plot}} \right\} \times 100$$

The results are shown in Table 9.

TABLE 9

| Compound No. | Dosage (g/are) | Growth inhibition percentage (%) | | | |
|---|---|---|---|---|---|
| | | Rice plant | Barnyardgrass | Broadleaved weed | Monochoria | Needle spikerush |
| 2 | 0.28 | 0 | 100 | 100 | 100 | 100 |
| | 0.14 | 0 | 100 | 100 | 100 | 85 |
| 10 | 0.12 | 0 | 100 | 100 | 100 | 100 |
| | 0.06 | 0 | 100 | 100 | 100 | 90 |
| F | 4 | 0 | 80 | 100 | 90 | 80 |
| | 2 | 0 | 40 | 60 | 60 | 30 |

What is claimed is:

1. A 2,4-dihalo-5-substituted phenyl-4,5,6,7-tetrahydro-2H-indazole compound of the formula:

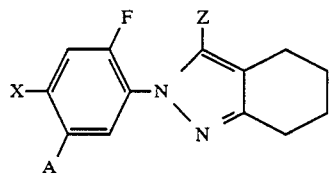

wherein X is a chlorine atom or a bromine atom, Z is a chlorine atom or a methyl group and A is an amino group, or a hydroxyl group.

2. A 2,4-dihalo-5-nitrophenyl-4,5,6,7-tetrahydro-2H-indazole compound of the formula:

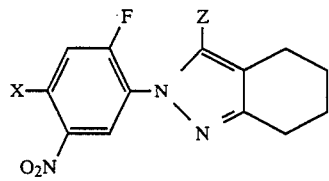

wherein X is a chlorine atom or a bromine atom and Z is a chlorine atom or a methyl group.

3. A 2,4-dihalo-5-hydroxyphenylhydrazine compound of the formula:

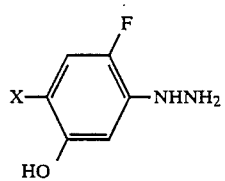

wherein X is a chlorine atom or a bromine atom.

* * * * *